(12) United States Patent
Cheng

(10) Patent No.: US 10,086,032 B2
(45) Date of Patent: Oct. 2, 2018

(54) **METHOD FOR PREPARING A *CAMELLIA NITIDISSIMA* CHI LIPID-LOWERING AND HYPOGLYCEMIC AGENT**

(71) Applicant: Shenzhen Violin Technology Co., Ltd., Shenzhen (CN)

(72) Inventor: Jinsheng Cheng, Foshan (CN)

(*) Notice: Subject to any disclaimer, the term of this patent is extended or adjusted under 35 U.S.C. 154(b) by 476 days.

(21) Appl. No.: 14/940,160

(22) Filed: Nov. 13, 2015

(65) Prior Publication Data
US 2016/0136224 A1    May 19, 2016

(30) Foreign Application Priority Data
Nov. 14, 2014   (CN) .......................... 2014 1 0647740

(51) Int. Cl.
*A61K 36/00* (2006.01)
*A61K 36/82* (2006.01)

(52) U.S. Cl.
CPC .......... *A61K 36/82* (2013.01); *A61K 2236/00* (2013.01)

(58) Field of Classification Search
CPC ..................................................... A61K 36/00
See application file for complete search history.

*Primary Examiner* — Qiuwen Mi
(74) *Attorney, Agent, or Firm* — Wayne & Ken, LLC; Tony Hom

(57) ABSTRACT

The present invention discloses a method for preparing a *Camellia nitidissima* Chi lipid-lowering and hypoglycemic agent. Active components such as tea polysaccharides, tea polyphenols, and flavones are extracted from *Camellia nitidissima* Chi and purified, which are then mixed with pharmaceutical excipients such as hydroxypropyl methyl cellulose, polyvinylpyrrolidone, and triethyl citrate to prepare various pills, tablets, capsules, granules, etc. including sustained release agents and controlled release agents. Thereby, clinical or health care medicine effects of the *Camellia nitidissima* Chi lipid-lowering and hypoglycemic agent are improved, a dosing frequency is reduced, interference of impurities with the medicine effect is eliminated, relative bioavailability and safety of the active components of the *Camellia nitidissima* Chi lipid-lowering and hypoglycemic agent in a human body are enhanced, and compliance of a patient is improved.

7 Claims, 1 Drawing Sheet

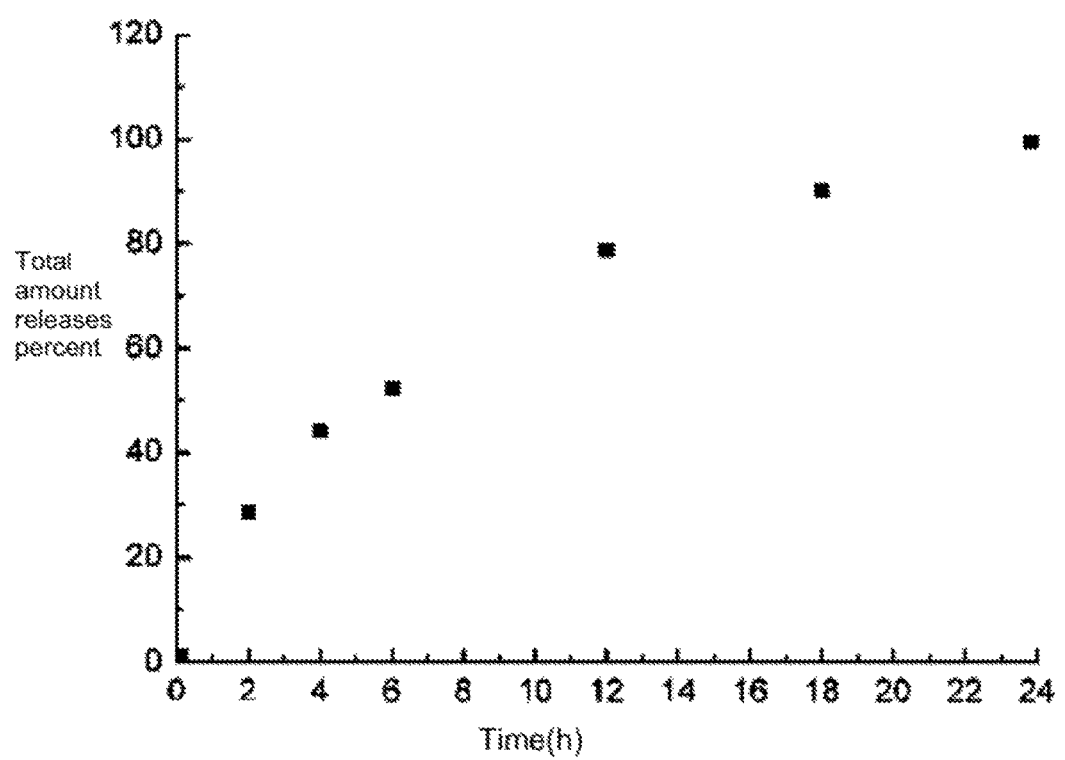

METHOD FOR PREPARING A *CAMELLIA NITIDISSIMA* CHI LIPID-LOWERING AND HYPOGLYCEMIC AGENT

CROSS-REFERENCE TO RELATED APPLICATIONS

This application is a continuation of, and claims priority to, Chinese Patent Application No. 201410647740.4 with a filing date of Nov. 14, 2014. The content of the aforementioned application, including any intervening amendments thereto, is incorporated herein by reference.

TECHNICAL FIELD

The present invention refers to the field of biotechnology, more particularly, to a method for preparing a *Camellia nitidissima* Chi lipid-lowering and hypoglycemic agent.

BACKGROUND OF THE PRESENT INVENTION

As a Chinese unique rare plant, *Camellia nitidissima* Chi has good reputation of "Giant Panda of Botany" and "Emperor in Theaceae". In civil history, it was recorded in *Compendium of Materia Medica*, and also in Local Chronicle of Gangdong and Guangxi that "*Camellia nitidissima* Chi, evergreen shrub, grow in wildemess", "the leaves and flowers of *Camellia nitidissima* Chi can be used for heat-clearing, the treatment of dysentery, lipid-removing and hypoglycemia". In folk of Guangdong and Guangxi area, *Camellia nitidissima* Chi is widely used to make tea or cook soup for clearing heat and removing toxicity, lipid-lowering and hypoglycemia, diuresis, dehydration and depressurization over thousands of years, so the lipid-lowering and hypoglycemic effect of *Camellia nitidissima* Chi has profound inherent foundation.

At present, there exist some theories and practice researches on *Camellia nitidissima* Chi lipid-lowering and hypoglycemic effect, for example, crude polysaccharide is primary separated by deproteinization and dialysis, then mice with hyperlipidemia are fed into the primary separated polysaccharide, experiment data shows high dose group, middle dose group and low does group of *Camellia nitidissima* Chi polysaccharide can all reduce TC, TG and LDL-C level of serum in the mice with hyperlipidemia dramatically and enhance mice with hyperlipidemia ratio. After two weeks of intragastric gavage, the TC level of serum of the mice can all reach normal level, and the effect is better than Xuezhikang capsule. Test results show *Camellia nitidissima* Chi polysaccharide is capable of obvious lipid-lowering function. (Lu Wei, Xiaoming Qin, Huajuan Lin, Enchuang Ning, Hong Yang. Study on Lipid-lowering Function of *Camellia Nitidissima* Polysaccharide); Enchuang Ning and co-workers feed Wistar rat with high-lipid diet for 15 days to make model of rat with hyperlipidemia, then intragastric gavage is performed with *Camellia nitidissima* Chi leaves aqueous extract respectively by 0.8 g/kg, 0.4 g/kg, and 0.2 g/kg, lovastatin (0.01 g/kg), the clinical lipid-lowering drug, is used for positive control. After 43 days of intragastric gavage, the serum is collected to test the total cholesterol (TC), tri glyceride (TG), high density lipoprotein cholesterol (HDL-C) and low density lipoprotein cholesterol (LDL-C). Results show both high dose group and middle dose group of *Camellia nitidissima* Chi leaves aqueous extract can reduce TC, TG and LDL-C content of serum in model rat with hyperlipidemia, the effect of which is equivalent to that of lovastatin, compared with the hyperlipidemia group, both the differences of high dose group and middle dose group have significance through test; high dose group and lovastatin can also enhance HDL-C content of serum in model rat with hyperlipidemia. So it shows the *Camellia nitidissima* Chi leaves aqueous extract have obvious lipid-lowering effect. (Enchuang Ning, Xiaoming Qin, Hong Yang. *Experimental Study on Lipid-lowering Function of Camellia Nitidissima Leaves Aqueous Extract. Journal of Guangxi university* (Nature and Science), 2004, 29(4), 350-352); Yonglin Huang and co-workers feed quail with high-lipid diet for 15 days to make model of quail with hyperlipidemia, then intragastric gavage is performed with 400 mg/kg *Camellia nitidissima* Chi leaves extract, fenofibrate tablets (20 mg/kg), the clinical lipid-lowering drug, is used for positive control, after 30 days of intragastric gavage, the serum is collected to test the total cholesterol (TC), tri glyceride (TG) content. Both the *Camellia nitidissima* Chi leaves extract and primary purified extract can reduce TC and TG content of serum in model quail with hyperlipidemia, while the ethanol extract can only reduce the TC content. *Camellia nitidissima* leaves extract have lipid-lowering effect and can perform enrichment with D-101 resin. (Yonglin Huang, Yueyuan Chen, Yongxin Wen, Dianpeng Li, Ronggan Liang, Xiao Wei. *Experimental Study on Lipid-lowering Function of Different Solutions and Primary Purified Camellia Nitidissima Leaves Extract. Lishizhen Med Mater Med Res,* 2009, 20(4), 776-777).

Diabetic mice models were established by intravenous injection of alloxan tetrahydrate by Xing Xia and co-workers, and the mice are divided into model group, metformin group, high dose group, middle dose group and low dose group of *Camellia nitidissima* Chi extract, while normal mice are the blank control group, then intragastric gavage is performed continually for 28 days and determine fasting blood-glucose before and after dosing of the 7th day, 14th day, 21th day and 28th day respectively, and after the final determination of fasting blood-glucose, 6 g/kg glucose solution is fed by gavage to all animals, then blood glucose level is determined after 30 min, 60 min and 120 min to inspect glucose tolerance levels of animals. Results show it can reduce the fasting blood-glucose (P<0.001) of diabetic mice dramatically after one week of dosing *Camellia nitidissima* Chi leaves extract, but only hypoglycemic effect of high dose group can continue, until 4 weeks of dosing, both high dose group and low dose group can reduce the blood-glucose (P<0.05) of diabetic mouse dramatically. In glucose tolerance experiment, *Camellia nitidissima* Chi leaves extract can inhibit the increase of blood glucose (P<0.001) after the meal, after 120 min of the meal, the blood glucose can be reduced to the level before the meal. A conclusion came to that *Camellia nitidissima* Chi leaves extract has lipid-lowering effect on alloxan-induced hyperglycemic mice due to low toxicity, so it may be used to help control blood glucose level of diabetic patients. (Xing Xia, Jiajun Huang, Zhiping Wang, Qin Wang, Weigao Pan. *Hypoglycemic Effect and Acute Toxicity of Camellia Nitidissima Leaves. Lishizhen Med Mater Med Res,* 2013, 5, F0003-F0004); diabetic mice models were established by intravenous injection of alloxan tetrahydrate by researchers, and the mice are divided into model group, metformin group, high dose group, middle dose group and low dose group of *Camellia nitidissima* Chi extract, while normal mice is the blank control group, then intragastric gavage is performed continually for 28 days, and after the final dosing, the fasting insulin levels are determined, change of the pancreas organization structure is observed by using HE staining, more-over, hepatic glycogen and hepatic glycogen level are determined. Data shows *Camellia nitidissima* Chi leaves extract can improve the insulin level (P<0.05) of diabetic mouse, relieve pancreas pathological lesion, and improve hepatic glycogen reserve (P<0.05) dramatically. Results show *Camellia nitidissima* Chi extract can improve pancreas structure and function, in this way, the lipid-lowering effect of *Camellia nitidissima* Chi extract can be played well. (Xing Xia, Chuanshen Pan, Lin Huang, Zhiping Wang, Qin Wang, Weigao Pan. (*Hypoglycemic Effect and Acute Toxicity of Camellia Nitidissima Leaves. Lishizhen Med Mater Med Res*, 2013, 12, 2863-2865).

In clinical study of Harbor Hospital of Beihai in Guangxi and Guangxi University in September 2003, they found *Camellia nitidissima* Chi products have good lipid-lowering and blood glucose regulating effect. There are 87 employees (including retired employees) in the test study in September, including many people with hyperglycemia and diabetic. The total cholesterol of chosen cases is more than 5.22 mmol/L (220 mg/dl), and triglyceride is more than 1.70 mmol/L (150 mg/dl). Patients aged 40 to 72, with 4-15 years medical history, all belong to secondary and tertiary "3-H diseases", that is, hyperlipidemia, hypertension and hyperlipidemia. After 30 days of taking *camellia nitidissima*, the subjective symptoms of 37 patients, occupying 88%, are improved obviously, symptoms like headaches, dizziness, tinnitus and precordium pain are disappeared, palpitation and compressive feeling are relieved, and weight is also reduced. The blood lipid is reduced generally. They are in good physical condition after 60 days, uncomfortable symptoms over years are disappeared, and the lipid is lowered to normal level. At the same time of lipid-lowering, the health condition turns good to varying degrees, many people insist on taking it throughout the year.

Above literatures or reports show that *Camellia nitidissima* Chi has unique advantages in lipid-lowering and hypoglycemic effect, the lipid-lowering effect is even better than the common medicine, clofibrate. The experimental animals which are fed into high-lipid food exist symptoms like deposition of aortic focal lipid, proliferation of fibrous tissue, increase of elastic lamina, and thickening of arterial wall; while for the experiment group fed into *camellia nitidissima*, above symptoms are smaller than control group obviously. So it demonstrates that *Camellia nitidissima* Chi has a remarkable effect on lowering lipid and cholesterol due to rich active components in *camellia nitidissima*, like tea polysaccharides. On the other hand, *Camellia nitidissima* Chi has a remarkable effect on hypoglycemia due to rich active components in *camellia nitidissima*, like tea polyphenols and flavones.

Many existing technologies study on the *Camellia nitidissima* Chi lipid-lowering and hypoglycemic pharmacology or lipid-lowering and hypoglycemic effect of *Camellia nitidissima* Chi aqueous extract or alcohol extract generally, while few technologies refer to the application fields like development and preparation of dosage forms of drug or health products. Besides, the best clinical or health care effect of lipid-lowering and hypoglycemic active components in *Camellia nitidissima* Chi can not be played to the fullest through the general study on lipid-lowering and hypoglycemic effect. In fact, only one or several kinds of key components in active components play the role of lipid-lowering and hypoglycemic effect, while others can not help to lower the lipid and reduce blood glucose, even to interfere curative effect or health care effect. For example, other components in *Camellia nitidissima* Chi like saponin, vanillin, ionone, phytol, α-spinasterol, arbricolin, hexadecyl-oxiran, myristic acid, α-Amyrin and β-Amyrin may greatly affect the lipid-lowering and hypoglycemic effect. In the development of pharmaceutical preparations, it is necessary to separate main lipid-lowering and hypoglycemic active components respectively and combine based on actual lipid-lowering and hypoglycemic clinical requirements to prepare various kinds of lipid-lowering and hypoglycemic agents.

SUMMARY OF THE PRESENT INVENTION

The purpose of the present invention is to solve problems above mentioned by offering a method for preparing a *Camellia nitidissima* Chi lipid-lowering and hypoglycemic agent with relative bioavailability and safety in a human body.

To achieve above purpose, the present invention employs the following technical solutions:

A method for preparing a *Camellia nitidissima* Chi lipid-lowering and hypoglycemic agent, comprising steps of:

1) Extracting and separating tea polysaccharides: the fresh *Camellia nitidissima* Chi leaves are smashed by high-speed tissue homogenizer after being cleaned, then the smashed leaves are placed into the triangular flask and fixed on reactor, the ultrasonic drug processor is started to perform extraction under solid to liquid ratio of 1:45-55, 75-85° C., 0.8-1.2 h, ultrasonic frequency of 53.2 kHz, and centrifugation is performed to the extract under 8000 r/min for 15 min, so the obtained supernatant is the crude extract of *Camellia nitidissima* Chi polysaccharide; 95% ethanol is added into the crude extract for 2-4 times to precipitate *Camellia nitidissima* Chi polysaccharide, then the obtained *Camellia nitidissima* Chi polysaccharide precipitation is dissolved by distilled water and constant volume can be performed, *Camellia nitidissima* Chi polysaccharide is prepared by recrystallization for 1-4 times, and phenol-sulfuric acid method is used to determine the contents of total sugar.

2) Extracting and separating tea polyphenols comprise following steps: the *Camellia nitidissima* Chi is smashed and screened through mesh size of 30, then dipped into 30% ethanol for 20 min, microwave extraction is performed for 20 min, the extract via hollow fiber membrane is separated by concentration with rotary evaporation and extraction with macro porous resin of XDA-200, water elution is performed to remove the impurity, 10% ethanol elution is also performed to remove impurity, in the successive step, 30% ethanol gradient elution is performed, the eluent is concentrated by rotary evaporation respectively, after freezing and drying, and the dried powder is obtained; finally, the tea polyphenols are prepared by three-time recrystallization; the content of tea polyphenols is determined based on detection method of tea polyphenols and catechins content of tea in GBIT 8313-2008, that is, the content of tea polyphenols=tea polyphenols quality in powder specimen/powder specimen quality)*100%

3) Extracting and separating flavonoid substance in *camellia nitidissima*: 10 g obtained $Fe_3O_4$ magnetic particles-PAMAM nano composites are added into 2.0 L *Camellia nitidissima* Chi leaves extract, ultrasonic extraction is conducted under 400 W, after extraction, the $Fe_3O_4$ magnetic particles-PAMAM nano composites together with the extraction of flavonoid substances are separated through magnetic separation, the separated $Fe_3O_4$ magnetic particles-PAMAM nano composites adsorbed with flavonoid substances are extracted for 3-5 times by the organic solvent, ethanol, the extract is mixed and the flavonoid substances in *Camellia nitidissima* Chi will be obtained by rotary evaporation, and flavonoid substance with higher purity can be obtained by three-time recrystallization, the ultraviolet spectrophotometer is used to determine the content of flavonoid substance.

One or combination of tea polysaccharides, tea polyphenols, and flavonoid substances are mixed with pharmaceutical excipients to prepare various ordinary pills, granules, powders, tablets, capsules etc.

As a further plan of the present invention, the mixing ratio of tea polysaccharides tea polyphenols and flavonoid substances is 0.1:0.1-1.5:0.1-1.5.

As a further plan of the present invention, the extraction condition of step 1 is under solid to liquid ratio of 1:45-55 75-85° C., 0.8-1.2 h, ultrasonic frequency of 53.2 kHz, and centrifugation is performed to the extract under 8000 r/min for 15 min, so the obtained supernatant is the crude extract of Camellia nitidissima Chi polysaccharide; 95% ethanol is added into the crude for 2-4 times extract to precipitate Camellia nitidissima Chi polysaccharide, then the obtained Camellia nitidissima Chi polysaccharide precipitation is dissolved by distilled water and constant volume is performed.

As a further plan of the present invention, pharmaceutical excipients include one or combination of hydrophilic gel materials, erodible framework materials and insoluble framework materials, of which the hydrophilic gel materials include one or combination of carboxyl methyl cellulose, hydroxypropyl methyl cellulose, calcium alginate, docusate sodium, guar gum, chitosan, polyvinyl alcohol, carbopol and DOW polyox water-soluble resin; the erodible framework materials include one or combination of octadecanol, cetyl alcohol, glyceryl behenate, stearic acid, glyceryl monostearate, cholesteryl stearate, camauba wax, hydroxypropyl methylcellulose phthalate, hydroxypropylcellulose, polyvininylpolyrrolidone, hydroxypropyl methylcellulose acetate succinate, polymethyl methacrylate, triethyl citrate, glyceryl triacetate and stearyl alcohol; the insoluble framework materials include one or combination of acrylic resin, polymethyl methacrylate and ethyecellulose.

As a further plan of the present invention, the hydrophilic gel materials are one or combination of hydroxypropyl methyl cellulose calcium alginate, polyvinyl alcohol, and DOW polyox water-soluble resin.

As a further plan of the present invention, the erodible framework materials are one or combination of octadecanol, glyceryl monostearate, carnauba wax, triethyl citrate, and stearyl alcohol.

As a further plan of the present invention, the insoluble framework materials include one or combination of acrylic resin and ethyecellulose.

As a further plan of the present invention, the Camellia nitidissima Chi lipid-lowering and hypoglycemic agent is further combined with one or combination lactase, starch, polyvinylpyrrolidone, tween, lauryl sodium sulfate, span, lecithin, urea, sucrose ester, polyoxyethylene aliphatate, polyoxyethylene aliphatic alcohol ether, poloxamer, sodium acid carbonate, sodium carbonate and basic magnesium carbonate, and the adhesive, excipient, flavoring agents, filler, wetting agent or lubricant is added by routine.

As a further plan of the present invention, the method is also applied to plants containing lipid-lowering and hypoglycemic active components as tea polysaccharides, tea polyphenois and flavones.

As a further plan of the present invention, the plants containing lipid-lowering and hypoglycemic active components such as tea polysaccharides, tea polyphenols and flavones include green tea, oolong, black tea, pu'er tea, dark tea, silkworm powder, Rhizome dioscoreae, Aralia chinensis, kiwi, Agaricus blazei murill, Balsam pear, cinnamon, wolfberry, Gynostemma pentaphyllum, buckwheat, Tartary buckwheat, oat, Halenia corni, celery, onion, Anoectochilus formosanus, dendrobium, Grateloupia filicina, spirulina, konjac, Gracilaria lemaneiformis, Folium mori, mulberry, Rhizoma polygonati, Litsea coreana leve, sweet basil, crocin, dandelion, propolis, Mitragyna rotundifolia kuntze, Polygonatum odoratum, Exocarpium benincasae, Polygala fallax hemsl, leaves of Diospyros kaki, Momordica charantia L., enteromorpha, Meretrix lusoria, pine needle, Cyclocarya paliurus, hazel's flower, Corn stigma, salvianolic acid, Toona sinensis, liquorice, Nigella glandulifera freyn, ulva, litchi pulp, yarrow. Allium macrostemon, Portulaca oleracea, cactus, pumpkin and lily.

Compared with the existing technologies, the advantage of the present invention is to solve problems, such as low use efficiency of Camellia nitidissima Chi lipid-lowering and hypoglycemic active components and the clinical or health care medicine effects due to interference of impurities by developing a method for Camellia nitidissima Chi lipid-lowering and hypoglycemic agent. Compatible drug compounds are mixed with pharmaceutical excipients based on optimum clinical or health care medicine effect to prepare lipid-lowering and hypoglycemic active components such as tea polysaccharides, tea polyphenols, and flavones in Camellia nitidissima Chi intovarious pills, tablets, capsules, granules, etc. Thereby, clinical or health care medicine effects of the Camellia nitidissima Chi lipid-lowering and hypoglycemic agent are improved to the fullest, a dosing frequency is reduced, interference of impurities with the medicine effect is eliminated, relative bioavailability and safety of the active components of the Camellia nitidissima Chi lipid-lowering and hypoglycemic agent in a human body are enhanced, and compliance of a patient is improved.

BRIEF DESCRIPTION OF DRAWING

FIG. 1 is a releasing curve of lipid-lowering and hypoglycemic biphase framework type controlled-release capsule of Camellia nitidissima Chi in embodiment 6.

DETAILED DESCRIPTION OF PREFERRED EMBODIMENTS

The technical proposals of embodiments are described below clearly and completely with reference to the embodiments. Obviously, it merely shows several specific embodiments of the present invention, rather than the whole embodiments. Other embodiments obtained by one of ordinary skilled in the art without creative work based on the embodiments of the present invention are all included within the protection scope of the present invention.

The technology of the present invention is that one or combination of lipid-lowering and hypoglycemic agent active components of Camellia nitidissima Chi such as tea polysaccharides, tea polyphenols and flavones is combined with one or combination of PEG, HMPC, PVP, mannitol, PEO-PPO to prepare dispersions, and the water solubility is improved, then HMPC, calcium alginate and other framework materials or other excipients are added to prepare Camellia nitidissima Chi lipid-lowering and hypoglycemic agent, the use efficiency of lipid-lowering and hypoglycemic active component of Camellia nitidissima Chi is improved, the dosing frequency is reduced, interference of impurities with the medicine effect is eliminated.

The *Camellia nitidissima* Chi lipid-lowering and hypoglycemic agents of the present invention can be ordinary pills, granules, powders, tablets, and capsules, and tablets include uncoated tablets, coated tablets, multilayer tablets or pressing coated tablets, and controlled release tablets such as membrane controlled release tablets, osmotic pump tablets, matrix tablets etc., or different formulations such as sustained release tablets, sustained release capsules, sustained release granules and sustained release pills.

The present invention proves that the pharmaceutical preparation overcomes the existing problems by excipients compatibility test, sink condition test and test of release in vitro, so it is good applied to clinic.

Excipients compatibility test: based on the test method of *Guidelines for Testing the Stability of Bulk Pharmaceuticals and Pharmaceutical Preparations* of Annex XIX C in Pharmacopoeia of China (2000), the main drugs and excipients are tested and identified as per the ration of 1:5. The test results show there is compatibility between main drugs and preferred excipients.

Sink condition test: one or combination of tea polysaccharides, tea it polyphenols, and flavones solid dispersion of whose quantity is triple in the prescription are put into the release medium and timing is started immediately, (release medium: 900 mL/cup distilled water, water temperature: 37.0±0.5° C., speed: 100 r/min), and the dissolving condition is observed, the oleanolic acid solid dispersion of six dissolution cups is completely dissolved at 25 min; and 10 mL solid dispersion is taken as the sampling at 30 min and filtration is performed, 20 mL subsequent filtrate is tested and calculated as per the method for determination of one or combination of lipid-lowering and hypoglycemic tablets, capsules, pills or granules etc of tea polysaccharides, tea polyphenols, and flavones in *camellia nitidissima*, a conclusion came to that above solid dispersion is completely dissolved into release medium from test results, which shows it meets sink condition.

Test of release in vitro: it is performed by the reference to test method of release in vitro in Annex of Pharmacopeia of China (2010). The second method of dissolution rate is used, release medium: 900 mL/cup distilled water, water temperature: 37.0±0.5° C., speed: 100 r/min, 10 mL is taken as the sampling each time at 2 h, 6 h, 12 h, 24 h respectively, and filtrated with 0.2 μm filter membrane timely, then release medium with same temperature and same volume is added, finally, the sample is tested. Subsequent filtrate into test tube with glass stopper is measured precisely, and then solvent is vaporized, 1 ml solution of sulfuric acid and methanol are added precisely according to the ratio of 7:3, being dissolved and shook well, being heated for 15 min under 60° C. water bath, then it is putted into ice-water bath immediately, 6 mol/L pretesting quantity sodium hydroxide solution is added to neutralize, (pretesting quantity: the volume of 6 mol/L sodium hydroxide solution to neutralize 1 ml solution of sulfuric acid and methanol according to the ratio of 7:3, the methyl red indicator solution is used as the indicator), then it is taken out to the room temperature, and transferred into 25 ml measuring flask with several times with ammonia-ammonium chloride buffer solution (pH=8.0), then it is diluted it to the granduation and shook well. Besides, tea polysaccharides (or tea polyphenols) reference substance (drying by phosphorus pentoxide overnight) are weighted precisely, and dissolved with 70% ethanol to prepare the solution with 0.4 mg for each 1 ml, then it is treated as per sample treatment method. It is measured and calculated by spectrophotometry.

Embodiment 1

Tea polysaccharides, tea polyphenols, and flavonoid substances are separated and purified as per above methods.

*Camellia Nitidissima* Oral Lipid-lowering Tablets: 160 mg specification, comprising:
Tea Polysaccharides: 40.0 mg
PVP: 40.0 mg
Docusate Sodium: 9.6 mg
Carboxyl Methyl Cellulose Cross-linked: 12.0 mg
Sodium Lauryl Sulfate: 1.6 mg
Microcrystalline Cellulose: 63.4 mg
Magnesium Stearate: 2.4 mg
Total: 160 mg In embodiments of the present invention, tea polysaccharides and PVP are dissolved into ethanol, spray drying is performed to the obtained solution to obtain nano-sized solid dispersion granules, the 50% diameter of which is 0.8 micrometer or smaller. Solid dispersion is further processed into tablets by mixing the diluents, glidants, and some lubricant, densifying the solid dispersion by pressing and then grinding, disintegrant and residue lubricant are added into ground granules and mixing, the lubricant granules are pressed into tablets, which can perform functional or non-functional film coating.

Embodiment 2

*Camellia Nitidissima* Oral Lipid-lowering Tablets: 160 mg specification, comprising:
Tea Polyphenols: 25.0 mg
Flavonoid substance: 15.0 mg
HPMCAS: 40.0 mg
Carboxyl Methyl Cellulose Cross-linked: 8.0 mg
Silicon Dioxide: 0.8 mg
Sodium Lauryl Sulfate: 0.8 mg
Microcrystalline Cellulose: 33.5 mg
Dicaldum Phosphate: 33.5 mg
Magnesium Stearate: 2.4 mg
Total: 160 mg In embodiments of the present invention, tea polyphenols, flavonoid substances and HPMCAS are dissolved into ethanol, spray drying is performed to the obtained solution to obtain nano-sized solid dispersion granules, the 50% diameter of which is 0.8 micrometer or smaller. Solid dispersion is further processed into tablets by mixing the diluents, glidants, and some lubricant, densifying the solid dispersion by pressing and then grinding, disintegrant and residue lubricant are added into ground granules and mixing, the lubricant granules are pressed into tablets, which can perform functional or non-functional film coating.

TABLE ONE

Release Data of *Camellia Nitidissima* Oral Lipid-lowering Tablet in Embodiment 2

| Sampling point | 2 h | 4 h | 6 h | 12 h | 18 h | 24 h |
|---|---|---|---|---|---|---|
| Releasing Quantity (100%) | 28.05% | 43.12% | 51.77% | 78.13% | 89.13% | 99.38% |

Embodiment 3

*Camellia Nitidissima* Oral Lipid-lowering Tablets: 160 mg specification, comprising:

Tea Polysaccharides: 20.0 mg
Tea Polyphenols: 20.0 mg
Flavonoid substance: 6.4 mg
Docusate Sodium: 6.6 mg
Sodium Lauryl Sulfate: 3.7 mg
PVP: 14.7 mg
Carboxyl Methyl Cellulose Cross-linked: 16.0 mg
Lactose: 60.6 mg
Polyvinylpyrrolidone Cross-linked: 11.2 mg
Magnesium Stearate: 0.8 mg
Total: 160 mg In embodiments of the present invention, tea polyphenols, flavonoid substances and docusate sodium are dissolved into ethyl acetate, spray drying is performed to the obtained solution to obtain nano-sized solid dispersion granules, the 50% diameter of which is 0.8 micrometer or smaller. The nano-sized solid granules are added into water solution of polyvinylpyrrolidone, and the obtained suspension is sprayed on lactose granules, then the dried and coated lactose granules are mixed drying with the carboxyl methyl cellulose cross-linked, polyvinylpyrrolidone cross-linked and sodium lauryl sulfate. Magnesium stearate is added into above mixture and then encapsulated.

Embodiment 4

*Camellia Nitidissima* Oral Lipid-lowering Capsules (1000 capsules), comprising
  Core Materials:
  Tea Polysaccharides: 44.6 g
  Polyvinylpyrrolidone (K30): 50 g
  Microcrystalline Cellulose: 30 g
  Coating Material:
  Ethyl Cellulose: 10 g
  Polyethylene Glycol: 2 g
  Castor Oil: 1 g
  Triethyl Citrate: 1 g
  Anhydrous Ethanol: appropriate amount Preparation technology: tea polysaccharides and polyvinylpyrrolidone (K15, K17, K30, K90 etc, K30 is the best) are mixed to prepare solid dispersion, it is screened through mesh size of 100, above dispersion and microcrystalline cellulose are mixed mechanically based on principle of equal incremental method, magnesium stearate is further added to mix and pressed into micro tablets, coating is performed with above coating material, the releasing rate is controlled by increment in weight for effective release, and then it is put into capsules, tea polyphenols: polyvinylpyrrolidone (K30)=0.1:0.83.

Embodiment 5

Tea polysaccharides, tea polyphenols, and flavonoid substances are separated and purified as per above method.
*Camellia Nitidissima* Hypoglycemic Pressing Coated Tablets: 605.7 mg, comprising:
  Tea Polyphenols: 87.8 mg
  Flavonoid substance: 80 mg
  Microcrystalline Cellulose: 278 mg
  Polyvinylpyrrolidone Cross-linked: 5 mg
  Polyvinylpyrrolidone: 10 mg
  HMPC: 3 mg
  Hydroxypropyl Methylcellulose Phthalate: 21.0 mg
  Magnesium Stearate: 6 mg
  Polyvinylpyrrolidone Cross-linked: 10 mg
  Polyvinylpyrrolidone: 10 mg
  Hydroxypropyl Methyl Cellulose: 4.5 mg
  Hydroxypropyl Cellulose: 4.1 mg
  Titanium Dioxide: 3.9 mg
  Talc: 2.4 mg
  Total: 605.7 mg In embodiments of the present invention, tea polyphenols, microcrystalline cellulose and polyvinylpyrrolidone are screened through mesh size of 35, and mixed for 5 min in high speed mixer to prepare mixture. Meanwhile, polyvinylpyrrolidone is dissolved into purified water to prepare adhesive solution (10 w/w %), then the adhesive solution is sprayed on the mixture to form granules, and drying.

Magnesium stearate is added into above granules and mixed for 4 min, the final mixture is pressed into tablets by rotary tablet press, the obtained tablets are regarded as inner core. Meanwhile, hydroxypropyl methyl cellulose and hydroxypropyl methylcellulose phthalate are dissolved and dispersed in 132 mg ethanol and 33 mg purified water to prepare coating solution, the inner core tablets are wrapped up with coating solution in HI-coater to form pressing coated sustained release coating inner core.

Flavonoid substances, microcrystalline cellulose, and polyvinylpyrrolidone cross-linked are screened through mesh size of 35, and mixed in high speed mixer, meanwhile, polyvinylpyrrolidone is dissolved into water to prepare adhesive solution. The adhesive solution and mixture of main ingredients are put into high speed mixer and kneaded. After the completion of kneading, the kneaded material is granulated with oscillator of mesh size of 20, magnesium stearate is added into the mixture and put into diplospondyly mixer for final mix.

The pressing coated tablets are prepared by pressing coated tablet machine, the pressing coated tablets include inner core coated tablets with tea polyphenols and outer combinations with flavonoid substances, meanwhile, hydroxypropyl methyl cellulose 2910, hydroxypropyl cellulose, titanium dioxide and talc are dissolved and dispersed in 132 mg ethanol and 33 mg purified water to prepare coating solution, the pressing coated tablets are wrapped up with coating solution in HI-coater to prepare *Camellia nitidissima* Chi lipid-lowering pressing coated tablets.

TABLE TWO

| Release Data of *Camellia Nitidissima* Oral Lipid-lowering Tablets in Embodiment 5 | | | | | | |
| --- | --- | --- | --- | --- | --- | --- |
| Sampling point | 2 h | 4 h | 6 h | 12 h | 18 h | 24 h |
| Releasing Quantity (100%) | 30.08% | 40.23% | 50.98% | 78.26% | 90.00% | 99.43% |

Embodiment 6

Tea polysaccharides, tea polyphenols, and flavonoid substances are separated and purified as per above methods.
Refer to FIG. 1, 429.9 mg lipid-lowering and hypoglycemic biphase framework type controlled-release capsules, comprising:
  Tea Polysaccharides: 70 mg
  Tea Polyphenols: 57.8 mg
  Flavonoid: 40.0 mg
  Microcrystalline Cellulose: 125 mg
  Kollicoat SR 30D: 25 mg
  Lactose: 52 mg
  Corn Starch: 25 mg
  Calcium Carboxymethyl Cellulose: 20 mg Polyvinylpyrrolidone: 7 mg
Polyethylene Glycol: 5 mg
Magnesium Stearate: 3 mg
Total: 429.9 mg In embodiments of the present invention, tea polysaccharides and microcrystalline cellulose are screened through mesh size of 35, mixed for 5 min in high speed mixer to prepare mixture. The Kollicoat SR 30D of BASF and mixture of main ingredients are put into high speed mixer and kneaded. After the completion of kneading, kneaded materials are granulated with oscillator of 20 mesh, and the granules are dried in dyer with 60° C. hot water, after the completion of drying, the granules are screened through 20 mesh again to prepare sustained release granules I.

Mixture of tea polyphenols and flavonoid substances, lactose, corn starch and calcium carboxymethyl cellulose are screened through 35 mesh, and mixed in the high speed mixer, meanwhile, the Kollicoat SR 30D of BASF and mixture of main ingredients are mixed into high speed mixer, and polyvinylpyrrolidone and polyethylene glycol are dissolved into water to prepare adhesive solution, the adhesive solution and mixture of min ingredients are kneaded, after the completion of kneading, kneaded materials are granulated with oscillator of 20 mesh, and the granules are dried in dyer with 60° C. hot water, after the completion of drying, the granules are screened again through 20 mesh.

The final products of above two steps are mixed in diplospondyly mixer, magnesium stearate is added into the mixture, then final mix is performed, the final mixture is put into powder feeder, then filled into capsules by encapsulating machine, thereby the lipid-lowering and hypoglycemic biphase framework type controlled-release capsules are prepared.

Embodiment 7

*Camellia Nitidissima* Oral Lipid-lowering and hypoglycemic Osmotic Pump Tablets (1000 tablets), comprising:
Core Tablets:
Tea Polysaccharides: 2 g
Tea Polyphenols: 3 g
Flavonoid substance: 1 g
Lactose: 60 g
Talc Powder: 2 g
5% PVP 80% Ethanol solution: appropriate amount
Coating Material:
Cellulose Acetate: 10 g
Polyethylene Glycol: 2 g
Triethyl Citrate: 1 g
Anhydrous Ethanol: appropriate amount Preparation technology: tea polyphenols, tea polysaccharides, flavonoid substances, and lactose are mixed mechanically based on principle of equal incremental method, appropriate binder is added to prepare soft wood, being granulated through mesh size of 18, and dried under 60° C., talc powder is further added to mix and press the mixed powder into tablets by tablet press, being coated with above coating solution until the thickness of coating film is within limits, the coating film is punched, then the osmotic pump tablet is obtained, which can achieve sustained release effect. Drugs: Lactose=1:3

It is obvious that the present invention is not limited to above embodiments for those skilled in the art, and the present invention can be realized by other embodiments without departing from the spirit or basic feature of the present invention. So the embodiments are demonstrative and non-restrictive, it is intended that the invention be limited only in terms of the appended claims, rather than above embodiments. So any variations that equivalent to the content and scope of claims shall fall into the protection scope of the present invention.

Besides, while the specification has described embodiments, it should be understood that not each embodiment merely include one independent technical proposal, it is for clearly description, the skilled in the art shall regard the specification as a whole, the technical proposals of each embodiments can be combined to form other embodiments.

I claim:

1. A method for preparing a *Camellia nitidissima* Chi lipid-lowering and hypoglycemic agent, comprising steps of:
    1) smashing fresh leaves of *Camellia nitidissima* Chi in a high-speed tissue homogenizer;
    placing the smashed leaves into a triangular flask and fixing the triangular flask on an ultrasonic processor at 8000 r/min and 53.2 kHz to centrifuge the smashed leaves under a solid to liquid ratio of 1:45-55 at 75-85° C. for 0.8-1.2 hours to produce a supernate;
    adding 95% ethanol to the supernate at a ratio of the supernate to the 95% ethanol of 1:2-4 to precipitate *Camellia nitidissima* Chi polysaccharides;
    dissolving the *Camellia nitidissima* Chi polysaccharides in distilled water; and
    recrystallizing the dissolved *Camellia nitidissima* Chi polysaccharides 1-4 times to produce tea polysaccharides;
    2) smashing *Camellia nitidissima* Chi and screening the smashed *Camellia nitidissima* Chi through 30 mesh; dipping the screened *Camellia nitidissima* Chi into 30% ethanol for 20 minutes;
    extracting the *Camellia nitidissima* Chi under microwave to produce a solution; separating the solution using a hollow fiber membrane and concentrating the separated solution through rotary evaporation;
    purifying the concentrated solution by macroporous resin XDA-200, elution with water, elution with 10% ethanol and gradient elution with 30% ethanol in order to produce a eluant;
    concentrating the eluant through rotary evaporation and freeze-drying the concentrated eluant to produce a powder; and
    recrystallizing the powder three times to produce tea polyphenols;
    3) adding $Fe_3O_4$ magnetic particle-PAMAM nano composites to a *Camellia nitidissima* Chi solution of 2.0 L and extracting the *Camellia nitidissima* Chi solution under ultrasound at 400 W for 1 hour;
    separating the $Fe_3O_4$ magnetic particle-PAMAM nano composites adsorbed with flavonoids and extracting the $Fe_3O_4$ magnetic particle-PAMAM nano composites adsorbed with flavonoids with ethanol 3-5 times to produce a solution;
    concentrating the solution by rotary evaporation to obtain flavonoids; and recrystallizing the flavonoids three times to purify the flavonoids; and
    4) mixing the tea polysaccharides, the tea polyphenols, and the flavonoids with pharmaceutical excipients to obtain the *Camellia nitidissima* Chi lipid-lowering and hypoglycemic agent.

2. The method of claim 1, wherein in step 4, the tea polysaccharides, the tea polyphenols and the flavonoids are mixed at a ratio of 0.1:0.1-1.5:0.1-1.5.

3. The method of claim 1, wherein in step 4, the pharmaceutical excipients are selected from the group consisting of hydrophilic gel materials, erodible framework materials and insoluble framework materials;

wherein the hydrophilic gel materials are selected from the group consisting of carboxyl methyl cellulose, hydroxypropyl methyl cellulose, calcium alginate, docusate sodium, guar gum, chitosan, polyvinyl alcohol, carbopol and DOW polyox water-soluble resin;

the erodible framework materials are selected from the group consisting of octadecanol, cetyl alcohol, glyceryl behenate, stearic acid, glyceryl monostearate, cholesteryl stearate, carnauba wax, hydroxypropyl methylcellulose phthalate, hydroxypropylcellulose, polyvininylpolyrrolidone, hydroxypropyl methylcellulose acetate succinate, polymethyl methacrylate, triethyl citrate, glyceryl triacetate and stearyl alcohol; and the insoluble framework materials are selected from the group consisting of acrylic resin, polymethyl methacrylate and ethylcellulose.

4. The method of claim 3, wherein the hydrophilic gel materials are at least one of hydroxypropyl methyl cellulose, calcium alginate, polyvinyl alcohol and DOW polyox water-soluble resin.

5. The method of claim 3, wherein the erodible framework materials are at least one of octadecanol, glyceryl monostearate, carnauba wax, triethyl citrate, and stearyl alcohol.

6. The method of claim 3, wherein the insoluble framework materials are at least one of acrylic resin and ethylcellulose.

7. The method of claim 1, wherein the *Camellia nitidissima* Chi lipid-lowering and hypoglycemic agent is further combined with one or more of lactase, starch, polyvinylpyrrolidone, tween, lauryl sodium sulfate, span, lecithin, urea, sucrose ester, polyoxyethylene aliphatate, polyoxyethylene aliphatic alcohol ether, poloxamer, sodium acid carbonate, sodium carbonate and basic magnesium carbonate.

* * * * *